United States Patent
Cuypers et al.

(10) Patent No.: US 10,343,309 B2
(45) Date of Patent: Jul. 9, 2019

(54) METHOD FOR MANUFACTURING A POLYMER SHEET FOR USE AS AN IMMOBILIZATION ELEMENT

(71) Applicant: ORFIT INDUSTRIES, Wijnegem (BE)

(72) Inventors: Steven Cuypers, Gravenwezel (BE); Bogdan Bogdanov, Schoten (BE)

(73) Assignee: ORFIT INDUSTRIES, Wijnegem (BE)

( * ) Notice: Subject to any disclaimer, the term of this patent is extended or adjusted under 35 U.S.C. 154(b) by 64 days.

(21) Appl. No.: 14/366,596

(22) PCT Filed: Dec. 20, 2012

(86) PCT No.: PCT/IB2012/057542
§ 371 (c)(1),
(2) Date: Jun. 18, 2014

(87) PCT Pub. No.: WO2013/093843
PCT Pub. Date: Jun. 27, 2013

(65) Prior Publication Data
US 2015/0000679 A1    Jan. 1, 2015

(30) Foreign Application Priority Data
Dec. 23, 2011    (BE) .................. 2011/0752

(51) Int. Cl.
*B29C 35/08*    (2006.01)
*A61F 5/37*    (2006.01)
(Continued)

(52) U.S. Cl.
CPC .......... *B29C 35/0805* (2013.01); *A61B 90/14* (2016.02); *A61B 90/18* (2016.02);
(Continued)

(58) Field of Classification Search
CPC ........ B29C 35/0805; B29C 2035/0827; B29C 35/0266; B29C 35/08
(Continued)

(56) References Cited

U.S. PATENT DOCUMENTS 4,056,421 A * 11/1977 Jarvis .................. B29C 35/0894
156/218
4,175,177 A * 11/1979 Potts ...................... C08G 63/08
264/456
(Continued)

FOREIGN PATENT DOCUMENTS

CN    1682673 A    10/2005
EP    0235500 B1    9/1987
(Continued)

OTHER PUBLICATIONS

International Search Report for PCT/IB2012/057542 dated Jun. 10, 2013.
(Continued)

*Primary Examiner* — Atul P. Khare
(74) *Attorney, Agent, or Firm* — Sughrue Mion, PLLC

(57) ABSTRACT

The present invention relates to a method for manufacturing a polymer sheet for use as an immobilization element, wherein the sheet is at least partly made of a polymer material comprising a polymer from the group of polycaprolactone, a copolymer of polyethylene with at least one α-olefin having 3-10 C atoms, or a mixture of two or more of the aforementioned polymers, a photo-initiator, and a photo-cross-linker, wherein the polymer sheet has a thickness of 1.0 to 5 mm and wherein the polymer sheet is at least partially cured by exposing to UV radiation for the at least partially cross-linking of the polymer.

17 Claims, 2 Drawing Sheets

(51) Int. Cl.

| | |
|---|---|
| *A61F 5/058* | (2006.01) |
| *C08J 3/24* | (2006.01) |
| *C08J 3/28* | (2006.01) |
| *A61L 31/04* | (2006.01) |
| *A61L 31/06* | (2006.01) |
| *A61L 31/14* | (2006.01) |
| *B29C 67/20* | (2006.01) |
| *A61B 90/18* | (2016.01) |
| *A61B 90/14* | (2016.01) |
| *A61L 15/12* | (2006.01) |
| *B29C 35/02* | (2006.01) |
| *A61B 17/00* | (2006.01) |
| *B29K 21/00* | (2006.01) |
| *B29K 23/00* | (2006.01) |
| *B29K 67/00* | (2006.01) |
| *B29K 105/00* | (2006.01) |
| *B29L 7/00* | (2006.01) |
| *B29L 31/00* | (2006.01) |

(52) U.S. Cl.
CPC .......... *A61F 5/05841* (2013.01); *A61F 5/37* (2013.01); *A61F 5/3707* (2013.01); *A61L 15/12* (2013.01); *A61L 31/048* (2013.01); *A61L 31/06* (2013.01); *A61L 31/146* (2013.01); *B29C 67/20* (2013.01); *C08J 3/244* (2013.01); *C08J 3/28* (2013.01); *A61B 2017/00526* (2013.01); *B29C 35/0266* (2013.01); *B29C 2035/0827* (2013.01); *B29C 2793/009* (2013.01); *B29C 2793/0045* (2013.01); *B29K 2021/006* (2013.01); *B29K 2023/08* (2013.01); *B29K 2067/046* (2013.01); *B29K 2105/0014* (2013.01); *B29K 2105/0085* (2013.01); *B29K 2995/0056* (2013.01); *B29L 2007/002* (2013.01); *B29L 2031/737* (2013.01); *C08J 2323/08* (2013.01); *C08J 2367/04* (2013.01)

(58) Field of Classification Search
USPC .................... 128/869–886; 264/494
See application file for complete search history.

(56) References Cited

U.S. PATENT DOCUMENTS

| | | | | |
|---|---|---|---|---|
| 4,238,522 | A | 12/1980 | Potts | |
| 4,240,415 | A | 12/1980 | Wartman | |
| 4,286,586 | A * | 9/1981 | Potts | A61F 13/04 427/2.1 |
| 4,863,768 | A * | 9/1989 | Ishio | B29C 35/08 426/127 |
| 5,063,613 | A * | 11/1991 | Brown | A61F 5/05866 128/880 |
| 5,500,163 | A * | 3/1996 | Ponnet | A61L 15/12 264/131 |
| 5,807,291 | A * | 9/1998 | Larson | A61F 5/058 602/7 |
| 6,210,788 | B1 * | 4/2001 | Cuypers | C08J 9/32 156/78 |
| 6,291,543 | B1 * | 9/2001 | Shah | A61L 29/14 522/134 |
| 7,802,576 | B2 * | 9/2010 | Cuypers | A61F 5/3707 128/845 |
| 7,867,180 | B2 * | 1/2011 | Cuypers | A61F 13/04 428/316.6 |
| 7,905,848 | B2 * | 3/2011 | Cuypers | A61F 13/04 128/845 |
| 8,916,016 | B2 * | 12/2014 | Marengo | B29C 35/0266 156/275.1 |
| 8,974,426 | B2 * | 3/2015 | Corcoran | A61M 25/0009 604/264 |
| 2002/0064653 | A1 | 5/2002 | Ladika et al. | |
| 2002/0065373 | A1 | 5/2002 | Krishnan | |
| 2004/0033380 | A1 * | 2/2004 | Bobovitch | B29C 55/02 428/515 |
| 2005/0222529 | A1 | 10/2005 | Cuypers et al. | |
| 2007/0004993 | A1 | 1/2007 | Coppens et al. | |
| 2008/0004368 | A1 | 1/2008 | Wang et al. | |
| 2008/0154164 | A1 * | 6/2008 | Sheehan | A61F 5/01 602/7 |
| 2009/0075542 | A1 * | 3/2009 | Cuypers | A61F 13/04 442/181 |
| 2013/0072839 | A1 * | 3/2013 | Cuypers | A61F 5/05841 602/7 |
| 2013/0123939 | A1 * | 5/2013 | Nauman | A61F 2/02 623/23.72 |

FOREIGN PATENT DOCUMENTS

| | | | | |
|---|---|---|---|---|
| EP | 0490854 | A2 * | 6/1992 | ............ B29C 35/10 |
| EP | 1 582 187 | A1 | 10/2005 | |
| JP | 2002504029 | A | 2/2002 | |
| JP | 2006257296 | A | 9/2006 | |
| JP | 2010163572 | A | 7/2010 | |
| WO | 93/00117 | A1 | 1/1993 | |
| WO | 9703130 | A1 | 1/1997 | |
| WO | 0222343 | A1 | 3/2002 | |
| WO | 2007/035875 | A2 | 3/2007 | |
| WO | 2011/113473 | A1 | 9/2011 | |

OTHER PUBLICATIONS

Communication dated Jul. 12, 2016, from the Japanese Patent Office in counterpart application No. 2014-548314.
Yoshii et al., "Crosslinking of poly(ε-caprolactone) by radiation technique and its biodegradability," Radiation Physics and Chemistry; vol. 57 (2000) pp. 417-420.
Gandhi et al., "Crosslinking of Polycaprolactone in the Pre-Gelation Region," Polymer Engineering and Science; vol. 28, No. 22 (Nov. 1988) pp. 1484-1490.
Yoshii, "Radiation Crosslinking of Polymer Materials," JAERI-Conf (2004-007) pp. 83-91.
Lee, "Thermoplastic Polyurethane Markets in the EU: Production, Technology, Applications and Trends," RAPRA Technology, Ltd. (Feb. 1998) 4 pages total.
Drobny, "Handbook of Thermoplastic Elastomers," Plastics Design Library, (2007) 7 pages total.
Cherry et al., "Practical Radiotherapy: Physics and Equipment," Second Edition, Wiley-Blackwell; (2009) 3 pages total.
Jacobs, "Splinting the Hand and Upper Extremity, Principles and Process," (2002) 2 pages total.
Bhowmick et al., "Handbook of Elastomers," Second Edition, Revised and Expanded; Marcel Dekker, Inc. (2001) 31 pages total.

\* cited by examiner

METHOD FOR MANUFACTURING A POLYMER SHEET FOR USE AS AN IMMOBILIZATION ELEMENT

CROSS REFERENCE TO RELATED APPLICATIONS

This application is a National Stage of International Application No. PCT/IB2012/057542, filed on Dec. 20, 2012, which claims priority from Belgian Patent Application No. 2011/0752, filed on Dec. 23, 2011, the contents of all of which are incorporated herein by reference in their entirety.

The invention relates to a method for manufacturing a polymer sheet for use as a non-invasive immobilization element for the immobilization of one or more body parts in a predetermined position and/or posture, as described in the preamble of the first claim.

Examples of immobilization elements for the immobilization of body parts are described for example in EP1854439, EP1537831, EP1582187 in the name of Orfit Industries. Immobilization elements are frequently used in numerous applications such as, for example, in rehabilitation, in orthopaedic applications, in the immobilisation of ligaments or bone structures that show injuries, with trauma or disease, where the immobilization element serves for supporting and immobilisation of ligaments and muscular structure in a predetermined position and/or posture. Furthermore, immobilization elements are extensively used in radiation therapy and diagnostic imaging. Especially in this latter application, an adequate immobilization of the body to be treated and an adequate and reproducible positioning of the body part undergoing treatment is of crucial importance in order to ensure that the radiation is directed at and limited to the body part to be treated, and that the risk of irradiating surrounding tissue is limited to a minimum. A reproducible positioning is also of the utmost importance in fractionated therapy, in which a part of the body, after predetermined time intervals, is exposed to irradiation. In this sense, it is of great importance that the immobilization element exhibits a high stability, by which is meant that the ability to move or reposition the body part, once immobilized, is limited to less than a few mm, preferably up to 1-2 mm or even less.

US 2008/0004368 discloses self-crosslinkable and photo-cross-linkable, biodegradable polymer materials, which, after injection into human tissue or bone to be repaired, are cured in situ in order to serve as a support for tissue and/or skeletal reconstruction. The method, described in US 2008/0004368 for the production of such materials, include the copolymerization of poly(propylenefumarate) with poly(caprolactone) diol, and provides a block polymer of poly(propylenefumarate) with poly(ε-caprolactone). The block copolymer is cross-linked by redox- or photoinitiation, with or without the addition of an additional cross-linking agent. In other words, the copolymer is self-crosslinkable, without the need of a cross-linking agent to be added and photo-cross-linkable in the presence of UV radiation. The relatively rigid poly(propylenefumarate) segment provides mechanical strength and crosslinkability while the poly(ε-caprolactone) segment provides flexibility for the self-cross-linking.

U.S. Pat. No. 6,291,543 relates to articles whose surface is cross-linked by exposure to UV radiation. The articles are formed from an elastoplastic material (such as a polyester, polyamide, polyurethane, etc.), a cross-linking agent (for example, triallyl cyanurate), which is cross-linkable by free-radical polymerization, and a source of free radicals (for example, benzophenone), which generates free radicals upon exposure to UV radiation. The article is particularly suitable for use in a catheter or other medical application. Only the top layer of the article is cross-linked, hence not the full thickness of the material. Due to the cross-linking of the surface, the hardness or rigidity of the article is increased, and said hardness or rigidity can be selectively provided to different parts of the article, by cross-linking the surface of certain parts of the article.

U.S. Pat. No. 6,709,742 relates to elastic fibres, consisting of a polyolefin, for example polyethylene, and a photo-initiator in an amount sufficient to cause at least a partial cross-linking of the polymer, if the fibre is exposed to UV-radiation. Articles made from fibres of said invention exhibit a good heat resistance and elasticity at high temperatures.

However, none of these publications discloses a method which enables to produce a polymer sheet of which the mechanical properties can be varied and/or controlled, not only of the sheet in the molten state, but also of the final immobilization element. Important characteristics of immobilization elements for immobilizing body parts are that they have the ability to capture precisely the position and/or posture of the body part to be immobilized and to limit the ability to move the body part within acceptable limits, once immobilized. For example, in applications such as imaging and radiotherapy, it is also important that the immobilization element allows for a reproducible positioning in time in a very precise manner. This is particularly important in the case of fragmented treatments. On the other hand, it is important that the polymer sheet is sufficiently flexible in order to ensure an adequate wear comfort.

The object of the present invention is to provide a method for producing a polymer sheet suitable for use as an immobilization element, or for the manufacture of immobilization elements, for the immobilization of one or more body parts.

This is achieved by the invention by a method comprising the technical features of the characterizing part of the first claim.

To this end, the method of the present invention is characterized in that a polymer sheet, having a thickness of 1.0 to 5.0 mm, which is at least partly made of a polymer material comprising a polymer from the group of polycaprolactone, a copolymer of polyethylene with at least one α-olefin with 3-10 C atoms, or a mixture of two or more of the aforementioned polymers, and a photo-initiator, is at least partially cured by exposure to UV radiation for the at least partial cross-linking of the polymer.

Within the scope of the present invention, with cross-linking is meant the cross-linking of a polymer material, but also the hardening of a polymer material.

The inventor has found that the use of UV radiation offers the possibility to vary and control the degree of cross-linking of the polymer sheet and hence, the mechanical properties of the polymer sheet after the cross-linking has been achieved. A higher degree of cross-linking usually leads to a polymer sheet with a higher toughness and rigidity, a higher modulus of elasticity in the molten state and less elasticity and a higher rigidity in the molten or softened state. When forming such a sheet in the molten or softened state to an immobilization element on the body part to be immobilized, this usually leads to a formed sheet with a higher thickness and better stability. A lower degree of cross-linking usually leads to a polymer with a lower toughness and rigidity, a lower modulus of elasticity in the molten state, a higher stretchability and a higher rigidity in the molten or softened state. When forming such a sheet in the molten or softened state to an immobilization element on the body part to be immobilized, this usually leads to a formed sheet of a smaller thickness. The present invention thus provides the possibility to control properties such as modulus of elasticity, elasticity and rigidness of the polymer sheet in the molten or softened state by controlling the degree of cross-linking. As a result, it is possible to vary and/or to control the thickness of the polymer sheet during its formation into an immobilization element in a molten or softened state, and therefore also the thickness of the polymer in the formed immobilization element.

The inventors have further found that the use of UV radiation offers important advantages compared to the use of γ-radiation, known from the state of the art. Where the use of γ-radiation leads to a uniform curing or cross-linking of the polymer material over the entire thickness of the polymer material, the use of UV-radiation provides the advantage that the penetration depth of UV radiation in the material can be controlled, and thus the degree of cross-linking or curing degree as a function of the penetration depth. This offers the advantage that the flexibility and rigidity of the recrystallized material, as well as the stability of the immobilization element and the comfort provided to the patient can be varied and controlled.

The method according to the invention is suitable for the manufacturing of polymer sheets, made of polymer materials which are transparent for visible light, as well as polymer sheets, made of polymer materials which are transparent for non-visible light. With polymers, transparent for UV radiation, such as copolymers of polyethylene, the UV penetration depth will usually be larger, and a more uniform degree of cross-linking as a function of the thickness and a higher uniformity in the mechanical properties over the entire thickness of the polymer will easily be realized.

Cross-linking by means of γ-radiation and electron beam cross-linking is usually implemented in expensive devices, especially provided for that purpose, and which are normally not found on the location where the polymer sheets or the immobilization elements are produced, making the production process slow and complex and inflexible.

Moreover, it is common to irradiate a pack of a large number of sheets with gamma-rays (see section above for symbol) in order to limit transport costs and irradiation time. In such a configuration, however, the different sheets are given a different dose of radiation. For example, sheets on the surface are more exposed to radiation than those that are located more in the middle of the pack. This has as a consequence that the different sheets, according to their mutual position and their position relative to the radiation source, exhibit a different degree of cross-linking, which is undesirable.

Cross-linking in the presence of peroxide often causes shrinkage and orientation of the polymer sheet when heating the sheet prior to forming the immobilization element over the body part. With the use of UV radiation, it is possible to treat the polymer sheets individually, on-site, and to control the degree of cross-linking of the individual sheets, taking into account the intended application, or on the other hand to simultaneously expose multiple sheets to UV radiation.

The method of the present invention further provides the possibility to reduce the UV penetration depth in polymers which are transparent for non-visible light, such as polycaprolactone, to the vicinity of the irradiated surface, such that a higher viscosity on the irradiated side of the polymer sheet can be obtained, and a higher elastic modulus in the molten state as a result of a larger degree of cross-linking, in comparison with the inside which is softer, and more thermo-formable, and which has a lower melting strength as a result of a lower degree of cross-linking.

The method of the present invention also offers the possibility to divide the polymer sheet into zones, and to subject different zones to a different degree of cross-linking. A particular embodiment of the present invention is therefore characterized in that the polymer sheet at least comprises a first and a second zone, wherein the first and second zone have a different degree of cross-linking.

Preferably, the polymer sheet is composed of a polymer material comprising
   a polymer from the group consisting of polycaprolactone, a copolymer of polyethylene with at least one α-olefin having 3-10 C atoms, or a mixture of two or more of the aforementioned polymers,
   a photo-initiator.

A polymer material which comprises polycaprolactone or a copolymer of polyethylene with at least one α-olefin having 3-10 C atoms, is particularly suitable for the manufacture of a polymer sheet for use as an immobilization element. These polymer materials are mouldable in the molten or softened state at low temperatures, tolerated by the body and the skin, such that the polymer sheet can directly be formed onto the body part to be immobilized. This makes the polymer sheet of the present invention particularly suitable for use as immobilization element in radiation therapy and diagnostic imaging, and in all other applications where a tight fit on the body part to be immobilized is of the utmost importance to provide an accurate positioning and repeatable re-positioning of the body part in the desired position, to enable a single treatment or an intermittent or fractionated treatment.

In the context of the present invention, with a photo-initiator is meant a chemical composition which, when exposed to UV light, generates radicals on the polymer chains and initiates cross-linking of the polymer. In the context of the present invention, a wide range of photo-initiators may be used. Preferably, the photo-initiator is selected from the group of benzoin, substituted benzoins such as benzoin ethyl ether, benzophenone, benzophenone derivatives, Michler's ketone alfa-hydroxyketone, benzil dimethyl ketal, isopropyl thioxanthane, dialkoxyacetophenones such as diethoxyacetophenone, acetophenone, benzil, and other derivatives and mixtures thereof. Benzophenone is particularly preferred.

The concentration of the photo-initiator in the polymer material can be varied within wide limits. The most favourable concentrations and ratios may be determined empirically by varying the composition and exposing the polymer sheet to UV radiation to obtain, for the intended application, the optimum physical and chemical properties of the at least partially cross-linked polymer material. In general, the concentration of photo-initiator is between 0.1 and 5.0 weight %, and preferably between 0.2 and 5.0 weight %, based on the weight of the polymer material.

Preferably, the polymer material also comprises an amount of a photo-cross-linker. Within the context of the present invention, with photo-cross-linker, a chemical composition is meant that, in the presence of a photo-initiator, accelerates and promotes the cross-linking of the polymer. This allows the production of a polymer sheet to be accelerated. A wide range of photo-cross-linkers, which, when generating free radicals, are able to link two or more polymer chains through the formation of covalent bonds, may be used in the present invention. Preferably, these photo-cross-linkers are polyfunctional, that is to say that they have two or more reactive functional groups which, when activated, are capable of forming a covalent bond with a functional group on the polymer. Photo-cross-linkers with a low melting temperature (<100-120° C.) and a good compatibility with polycaprolactone and a copolymer of polyethylene with at least one α-olefin having 3-10 C atoms, are preferred. In this context, triallyl cyanurate is particularly preferred. Other examples of suitable photo-cross-linkers may be selected from the group of polyfunctional vinyl or allyl compounds such as triallyl cyanurate, triallyl isocyanurate, pentaerthritol tetramethacrylate, ethylene glycol, dimethacrylate, diallyl maleate, dipropargyl monoallyl cyanurate, and other derivatives and mixtures thereof.

The concentration of the photo-cross-linker in the polymer material may be varied within wide limits, but preferably ranges between 0.01 and 2.0 weight %, based on the weight of the polymer material.

The polymer material may also comprise other components to change the mechanical properties of the polymer sheet, if this is of interest for the intended application.

Preferably, the at least one α-olefin with 3-10 C atoms is at least one selected from the group consisting of 1-butene and 1-octene. The inventors have found that these plastic materials are mouldable at a low temperature. This renders the polymer sheet of the present invention particularly suitable for use in radiation therapy and diagnostic imaging and in all other applications where a precise repositioning of the immobilization element in intermittent treatment is of the utmost importance. In addition the polymer sheet offers, for use as immobilization element, more comfort to the patient, because it feels soft to the skin and has a higher flexibility and lower rigidness, even after complete crystallization, in comparison with the already known immobilization elements. As a result of the reduced rigidness, the material can easily be cut with a good and smooth finish of the edges with conventional tools such as scissors and knives.

The polymer material comprising polycaprolactone or a copolymer of polyethylene with at least one α-olefin having 3-10 C atoms, a photo-initiator and a photo-cross-linker, can be prepared in any manner known to the skilled person, for example, by mixing or combining the ingredients by mechanical stirring, by a sonication treatment, or by means of a melt mixer. Manufacturing a polymer sheet on the basis of this composition may be done by any technique deemed suitable by the skilled person. Preferably, the forming of the polymer material into a sheet is done by means of extrusion, in particular flat extrusion.

In the process of the present invention, the polymer sheet prior to the exposure to UV radiation is preferably cut into a desired shape. This offers the advantage that the waste material is not cross-linked and can be recovered for recycling. Since the polymer material is relatively expensive, and an average of up to 30% of the material is lost as waste when cutting and perforating, this is an important advantage. Moreover, it was found that the cutting of the polymer sheet and the cross-linking of the sheet can be combined in a process, wherein, in a first step, the polymer sheet is cut into the desired shape, and subsequently exposed to UV radiation for cross-linking of the polymer sheet. It was found that the time, required for cutting the sheet into the desired shape, can be tailored to the time required for cross-linking the polymer to the desired degree of cross-linking.

If desired, this can be carried out in an automated process, optionally supplemented by a step in which the polymer sheet is entirely or partly perforated. Perforation may be carried out before or after the exposure to UV-radiation. Usually, perforation is carried out prior to exposure to UV radiation to better achieve a better uniformity in the cross-linking and to allow recycling of perforation material.

Perforation may extend over the entire sheet, or may be limited to specific areas in the surface direction of the polymer sheet. Perforations will usually extend through the entire thickness of the sheet. The perforations may be applied randomly or according to a certain pattern. The dimensions of the perforations in the polymer sheet will usually range between 0.5 and 3.0 mm, preferably between 1 and 2 mm. According to the invention, all perforations may approximately have the same dimensions, or perforations of varying dimensions may be used at random or in different zones. The latter offers the possibility to locally change the elasticity of the polymer sheet. The presence of perforations offers many advantages, including the fact that the immobilization element is lighter and allows evaporation of moisture through the immobilization element.

The polymer sheet, used in the process of the present invention, preferably has a thickness which is adapted to the intended use. When using the polymer sheet as an immobilization element, the thickness of the polymer sheet preferably ranges between 1.0 and 5.0 mm. Often a thickness of about 1.6-3.2 mm is used. With such a thickness, the desired degree of cross-linking can be obtained by exposing the polymer sheet either on one side, or on both sides, to UV radiation.

The duration of the irradiation with UV, and the energy of the UV radiation source, may be varied within wide limits, and is preferably chosen such that the desired degree of cross-linking is achieved without degradation of the polymer sheet to occur. For the manufacture of a polymer sheet according to the invention, the sheet is exposed to UV radiation, preferably for a period of time of 30 seconds to 1 hour at a radiation power of 10 watts to about 500 watts. It is to be expected that with a higher radiation power, a shorter period of time is required. The skilled person is capable of matching the radiation intensity and duration to the intended degree of cross-linking, taking into account the thickness of the polymer sheet and the transparency of the sheet for UV radiation. The skilled person may choose to irradiate the polymer sheet on one surface, or on both surfaces, facing each other.

In the context of the present invention, with UV radiation is meant that the wavelength of the radiation ranges between 150 and 700 nm, preferably between 100 and 450 nm, more preferably between 280 and 400 nm. At a wavelength of the UV radiation which ranges between 100 and 450 nm, the photo-initiators which are preferred within the scope of the present invention, attain their maximum efficiency. The most appropriate wavelength is chosen taking into account the thickness of the polymer sheet, the nature of the polymer material and the nature of the photo-initiator. It is generally known that UV radiation with a longer wavelength penetrates more deeply, and hence allows cross-linking a thicker polymer sheet. Irradiation with UV light may be carried out on one surface of the polymer sheet, or on both surfaces, facing each other.

Suitable UV sources comprise conventional UV lamps, typically Hg lamps, which span a wide continuous band of the UV spectrum, usually between 200 and 450 nm. They may develop high powers, but this is accompanied by a significant warm-up, which can lead to the melting of the polymer sheet. Therefore, it may be necessary to cool the polymer sheet, for example by means of a cold air or gas flow. LED lamps have the property that they span a narrow discrete band of the UV spectrum, often in the wavelength range of 365 or 395 nm. LED lamps have a lower power such that cross-linking is slower, but it is better controllable. A lower power can be overcome by decreasing the distance between the light source and the polymer sheet, or by using the light source in combination with a photo-initiator with a high efficiency. The skilled person will take into account, when selecting the source of the UV radiation, the requirements of the application. Suitable LED lamps are commercially available from various suppliers.

The present invention also relates to a non-invasive immobilization element obtained by the method described above.

The present invention further relates to a non-invasive immobilization element for the immobilization of one or more body parts in a predetermined position, wherein the immobilization element comprises a sheet which is at least partly made from a polymer material, comprising an at least partially cross-linked polymer selected from the group of polycaprolactone, a copolymer of polyethylene with at least one α-olefin having 3-10 C atoms, or a mixture of two or more of the aforementioned polymers, and a photo-initiator, wherein the polymer sheet has a thickness of 1.0 to 5.0 mm. Further technical characteristics of the immobilization element are as described above.

As described above, in a preferred embodiment, the polymer sheet has a degree of cross-linking which decreases from a surface of the polymer sheet in the thickness direction of the polymer sheet.

As described above, in another preferred embodiment, the polymer sheet comprises at least a first and a second zone, wherein the first and second zone have a different cross-linking.

The invention will be further elucidated with reference to the attached figures and the description of the figures below.

Figure 1:
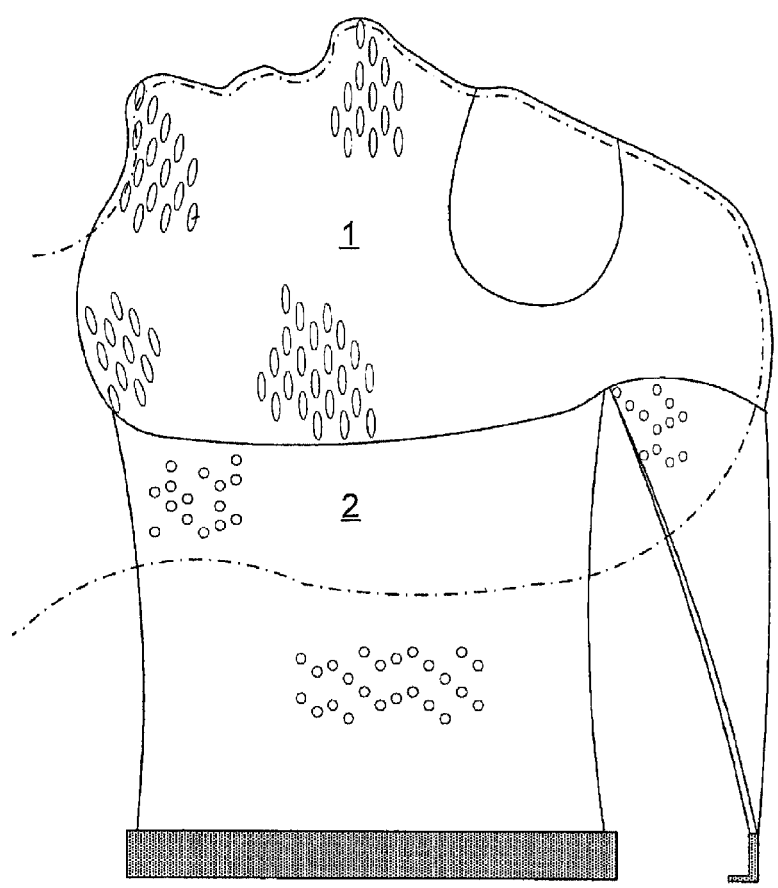
FIG. 1 shows an example of a non-invasive immobilization element according to the invention, in particular a mask for immobilising the head of a patient.

The immobilization element as shown in FIG. 1, is placed on the skin of the body part to be immobilized of the patient in such a way that the body part is enclosed by the immobilisation element, and is incorporated therein. The edges of the immobilization element are attached to a table on which the patient is located in order to immobilize the body part in the desired posture and the desired position.

Figure 2:
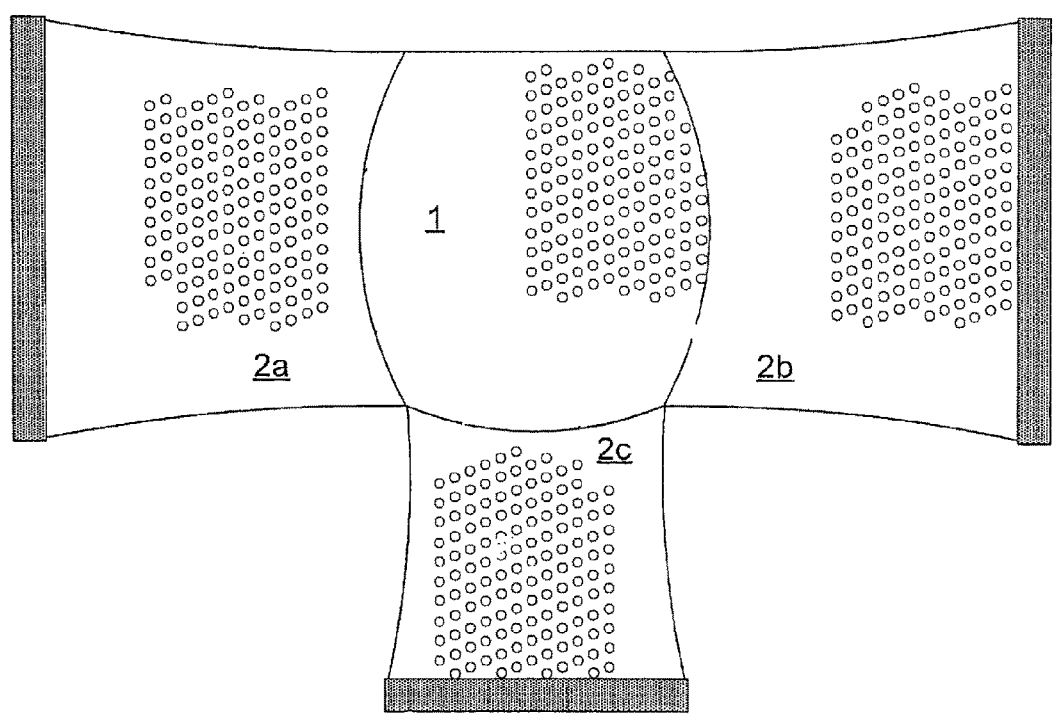
FIG. 2 shows a polymer sheet cut in a shape for the manufacture of the mask shown in FIG. 1.

The polymer sheet shown in FIG. 2 exhibits a mask zone 1 which is intended to cover the face of the head, a first, second and third connection zone 2a, 2b and 2c which are intended for connecting the mask zone with a support on which the patient is located and thus to oppose movement of the head as good as possible and to limit it to a maximum of 1-2 mm.

Within the context of the present invention, the mask zone 1 and the connection zones 2a, 2b, 2c may show the same or a different degree of cross-linking. The connection zones 2a, 2b, 2c may exhibit a mutually similar or a different degree of cross-linking. In a preferred embodiment, the connection zones 2a, 2b, 2c have a higher degree of cross-linking, and the mask zone 1 has a lower degree of cross-linking. For the manufacture of an immobilization element, the polymer sheet is heated to a temperature in the range of the melting or softening temperature. The thus melted or softened sheet is applied to the body part to be immobilized and formed thereon, preferably in such a way that the sheet adopts as weir as possible to the contours of the body part to be immobilized.

In the context of the present invention, it is also possible to divide one or more connection zones into two or more zones, and to give different zones a different degree of cross-linking.

A lower degree of cross-linking in the mask zone 1 leads to a polymer with a lower toughness and rigidity, lower modulus of elasticity and a higher rigidity and lower stretchability in the molten or softened state. The higher stretchability offers the possibility to significantly reduce the thickness of the polymer sheet in comparison with a sheet with a higher degree of cross-linking, and thus to provide a mask zone 1 with a somewhat higher flexibility, even after cooling and crystallization, and a smaller thickness.

In the context of the present invention, it is further possible to divided the mask zone 1 into two or more zones, and to give different zones a different degree of cross-linking.

A higher degree of cross-linking in the connection zones 2a, 2b, 2c leads to a higher toughness and rigidity, a higher elasticity modulus and lower stretchability in the molten or softened state. The lower stretchability of the connection zone counteracts stretching of the connection zone and usually leads to connection zones with a higher thickness, which is rigid and provides stability to the immobilization element. Thus, it is possible to reduce the ability of the patient to move with respect to the mask to a minimum and at the same time to maximize comfort for the patient.

Dividing the polymer sheet into two or more zones, provides the ability to individually control the degree of cross-linking of the zones, and to control the mechanical properties of the individual zones, taking into account the function they perform in the immobilization element.

In the example shown, both the mask zone 1 and the connection zone 2a, 2b, 2c are perforated. Within the scope of the present invention, the mask zone 1 may or may not be perforated, and the connection zones 2a, 2b, 2c may or may not be perforated. The mask zone 1 may have the same degree of perforation and perforation pattern as the connection zones 2a, 2b, 2c, or a different one. The connection zones 2a, 2b, 2c may exhibit the same degree of perforation and perforation pattern or a different one.

Within the mask zone, a uniform perforation can be used. However, it is also possible to divided the mask zone into zones which have a different degree of perforation. It is further possible to control the size of the perforations in each zone, as well as the number of perforations that is applied and the pattern. Thus, the possibility is offered to divide the mask zone into zones which have different perforation rate.

By analogy, within one connection zone, a uniform perforation to be applied, or the connection zone can be divided into further zones, which have a different degree of perforation. Thereby, the size of the perforations in each zone to be controlled, as well as the number of perforations applied and the perforation pattern.

The adjustability of the degree of cross-linking and the degree of perforation makes it possible to vary and to control the mechanical properties of an immobilization element within wide limits. The division into zones allows the mechanical properties of each zone of the immobilization element to match the function performed by that zone.

The invention will be further described with reference to exemplary embodiments below.

EXAMPLE 1

Polymer sheets having a composition as listed below were prepared by cross-linking by exposure to UV radiation of a single sheet of polymer material which comprises either polycaprolactone (Capa), obtained from Perstorp UK Ltd, or a polyolefin elastomer, obtained from Dow, as well as a photo-initiator (benzophenone), obtained from Ciba, a photo-cross-linker (TAC) and a colour master batch. The composition of the polymer sheets is shown in Table 1. Table 1 shows the composition of a sample containing polycaprolactone (Capa), TAC and benzophenone, and a sample that contains a polyolefin elastomer, TAC and benzophenone, as well as a colour master batch.

The polymer sheets were manufactured by extruding the Capa or the polyolefin elastomer together with the photo-initiators, the photo-cross-linker in a ZSK 18 twin screw extruder (Coperion). The polymer material that is obtained in this way, was formed into a sheet by means of press moulding, using an hydraulic press of Agila model PE30.

The polymer sheets were cross-linked by exposure to UV radiation. For this purpose, use was made of UV lamps with a power of 18 W at a wavelength of 370 nm. The duration of the exposure to the UV radiation for the different polymer sheets is shown in Tables 2 and 3.

The degree of cross-linking of the polymer sheets was assessed by means of two measuring methods: 1) oscillation rheometry 2) RTS (resistance to stretch). The oscillation rheometry was performed with an Anton Paar Rheometer MCR 300. With the oscillation rheometer, used at a frequency of 0.01 to 10.0 Hz for a sample with standard dimensions, cut from the polymer sheet, the complex viscosity, the storage modulus and the loss modulus were determined, which increase as a function of the degree of cross-linking of the polymer sheet and therefore allow to estimate the degree of cross-linking. The measurements were carried out at a temperature of 70° C. RTS (resistance to stretch) is a method to estimate the degree of cross-linking of the polymer sheet by: (a) cutting a sample with standard dimensions from the polymer sheet, (b) heating the sample in hot water (65° C.), for 3 min., (c) securing one end of the sample with a clamp and providing the other end with a standard weight, (d) stretching the molten sample under the force of gravity and cooling to room temperature, (e) the value of the length of the stretched sample (cm) is the value of the RTS (cm) (f), the shorter the stretched sample, the higher the degree of cross-linking is. The results for the oscillation rheometry measurements are shown in Table 2 and the results for the RTS measurements in Table 3.

TABLE 1

Composition of the polymer samples.

| | Composition (%) |
|---|---|
| Sample 1 | |
| Capa | 83.5 |
| TAC Master batch | 12.0 |
| Colour Master batch | 3.0 |
| Benzophenone | 1.5 |
| Sample 2 | |
| Polyolefin elastomer | 85.0 |
| TAC Masterbatch | 12.0 |
| Benzophenone | 3 |

TABLE 2

Results of the oscillation rheometry measurements for the polymer samples.

| | Thickness (mm) | Curing (hours) | Comp. visc. (Pa · s) | Storage Mod. (Pa) | Loss Mod. (Pa) |
|---|---|---|---|---|---|
| Sample 1 | 1.2 | 0.0 | 1010 | 658 | 742 |
| | 1.2 | 2.0 | 2600 | 677 | 1630 |
| | 1.2 | 6.0 | 2910 | 824 | 1800 |
| Sample 2 | 2.0 | 0.0 | 5020 | 2220 | 2600 |
| | 2.0 | 1.0 | 7290 | 4100 | 2790 |
| | 2.0 | 2.0 | 10100 | 6180 | 2990 |

TABLE 3

Results of the RTS (resistance to stretch) measurements for the polymer samples.

| | Thickness (mm) | Curing (hours) | RTS (cm) |
|---|---|---|---|
| Sample 1 | 1.2 | 3 | 180 |
| | 1.2 | 8 | 88 |
| Sample 2 | 2.0 | 0.25 | 5.27 |

The invention claimed is:

1. A method for manufacturing a non-invasive immobilization element for immobilizing one or more body parts in a predetermined position, the method comprising:
   providing a polymer sheet having a thickness of 1.0 to 5.0 mm, the sheet at least partly made from a polymer material selected from the group consisting of polycaprolactone, a copolymer of polyethylene with at least one α-olefin having 3-10 C atoms, or a mixture of two or more of the aforementioned polymers, and the sheet additionally comprising a photo-initiator and photo-cross-linker; and
   at least partly curing the sheet by exposing both sides of the polymer sheet to UV radiation so as to at least partially cross-link the polymer material thereof, a penetration depth of the UV radiation into the sheet being controlled during the exposing so as to vary a degree of the cross-linking as a function of the penetration depth so that the sheet transitions from a more viscous cross-linked exterior at each of said sides having a higher cross-linking degree to a softer cross-linked interior having a lower cross-linking degree between each of said sides.

2. The method according to claim 1, wherein as a result of the varying cross-linking degree, the exterior of the sheet at each of said sides has a higher elastic modulus than the interior of the sheet.

3. The method according to claim 1, wherein the exposure is at a radiation power of 10 to about 500 watts for 30 seconds to 1 hour.

4. The method according to claim 1, further comprising directly shaping the at least partly cured sheet onto a body part at low temperatures so as to immobilize the body part.

5. The method according to claim 4, wherein the at least partly curing takes place on site prior to said directly shaping.

6. The method according to claim 1, wherein the immobilization element is for immobilizing the head of a patient during radiation therapy or diagnostic imaging.

7. The method according to claim 6, wherein the sheet comprises a mask zone and connection zones, each of the connection zones being separated along a length and/or width of the sheet, and wherein the connection zones have a higher degree of cross-linking than the mask zone.

8. The method according to claim 1, wherein the sheet comprises perforations of varying dimensions at random or in different zones of the sheet so as to locally change elasticity of the sheet.

9. The method according to claim 1, wherein the sheet, prior to the exposure to UV radiation, is cut into a desired shape.

10. The method according to claim 1, wherein the polymer sheet has an edge, and wherein the edge, prior to the exposure to UV radiation, is not perforated.

11. The method according to claim 1, wherein the UV radiation has a wavelength between 100 and 450 nm.

12. The method according to claim 1, wherein a UV radiation source supplying the UV radiation is selected from an LED light source or a conventional UV light source.

13. The method according to claim 1, wherein the at least one α-olefin with 3-10 C atoms is at least one selected from the group consisting of 1-butene and 1-octene.

14. The method according to claim 1, wherein the photoinitiator is one or more selected from the group consisting of benzoin, substituted benzoins, benzophenone, benzophenone derivatives, Michler's ketone alfa-hydroxyketone, benzil dimethyl ketal, isopropyl thioxanthane, dialkoxyacetophenones, acetophenone, benzil, and derivatives of the aforementioned compounds.

15. The method according to claim 14, wherein the substituted benzoin is benzoin ethyl ether.

16. The method according to claim 1, wherein the photo-cross-linker is one or more selected from the group consisting of polyfunctional vinyl or allyl compounds and derivatives thereof.

17. The method according to claim 16, wherein the polyfunctional vinyl or allyl compound is one or more selected from the group consisting of triallyl cyanurate, triallyl isocyanurate, pentaerthritol tetramethacrylate, ethylene glycol, dimethacrylate, diallyl maleate, and dipropargyl monoallyl cyanurate.

* * * * *